United States Patent [19]

Snyder

[11] 3,961,073

[45] June 1, 1976

[54] ANTIDEPRESSANT

[75] Inventor: Solomon H. Snyder, Baltimore, Md.

[73] Assignee: Nelson Research & Development Company, Irvine, Calif.

[22] Filed: July 1, 1975

[21] Appl. No.: 592,101

Related U.S. Application Data

[63] Continuation-in-part of Ser. No. 454,243, May 17, 1974, abandoned.

[52] U.S. Cl. .................................................. 424/325
[51] Int. Cl.² ......................................... A61K 31/13
[58] Field of Search .................................... 424/325

[56] References Cited
UNITED STATES PATENTS 2,997,422  8/1961  Tedeschi............................. 424/330

OTHER PUBLICATIONS

Kaiser et al., J. Medicinal & Pharmaceutical Chemistry, 5, 1243 (1962).

Primary Examiner—Stanley J. Friedman
Attorney, Agent, or Firm—Martin A. Voet

[57] ABSTRACT

A method for treating depression in humans by administering to depressed humans a composition containing an effective amount of the (−) enantiomer of trans-2-phenylcyclopropylamine or a pharmaceutically acceptable acid addition salt thereof, said composition being substantially free of (+) trans-2-phenylcyclopropylamine.

10 Claims, No Drawings

ANTIDEPRESSANT

REFERENCE TO EARLIER FILED APPLICATION

This application is a Continuation-in-Part of U.S. Ser. No. 454,243 filed May 17, 1974, now abandoned.

BACKGROUND OF THE INVENTION

1. Field of the Invention

The invention relates generally to a method of treating depression in human beings. More particularly, the present invention relates to a method of temporarily alleviating the symptoms of depression in humans being while minimizing side effects such as hypertension.

2. Background of the Prior Art

Inhibition of the enzyme monoamine oxidase is associated with compounds having usefulness in the treatment of clinical symptoms of depression. U.S. Pat. No. 2,997,422 discloses that the trans isomer of 2-phenylcyclopropylamine is a potent inhibitor of monoamine oxidase. However, the clinical usage of trans-2-phenylcyclopropylamine and other monoamine oxidase inhibitors has been markedly restricted in recent years because of potential side effects, e.g. hypertension thought to be associated with monoamine oxidase inhibition. These hypertensive and other side effects are thought to be caused by the action of toxic amines, such as tyramine, a toxic amine found in ripe cheese, which are not broken down in the body due to the inhibition of monoamine oxidase by the antidepressant compounds.

It is also known that trans-2-phenylcyclopropylamine may be resolved into its (+) and (−) enantiomers, Kaiser et al, "2-Substituted Cyclopropylamines", Journal of Medicinal and Pharmaceutical Chemistry, 5, 1243 (1962). It has also been shown that there is a differential activity of the (+) and (−) enantiomers of trans-2-phenylcyclopropylamine in rat brain synaptosomes, Horn and Snyder, "Steric Requirements for Catecholamine Uptake by Rat Brain synaptosomes: Studies with Rigid Analogues of Amphetamine", Journal of Pharmacology and Experimental Therapeutics, Vol. 180, No. 3 (1972).

SUMMARY OF THE INVENTION

It has now been discovered that the (−) enantiomer of trans-2-phenylcyclopropylamine may be used to temporarily alleviate the symptoms of depression in human being with minimal side effects such as hypertension.

The present invention relates to a method for temporarily alleviating the symptoms of depression in humans comprising administering to humans suffering from depression a composition comprising an effective amount of a compound selected from the group consisting of the (−) trans-2-phenylcyclopropylamine and a non-toxic pharmaceutically acceptable acid addition salt thereof, said composition being substantially free of (+) trans-2-phenylcyclopropylamine.

DETAILED DESCRIPTION OF THE INVENTION

The active compound in the present invention is the (−) enantiomer of trans-2-phenylcyclopropylamine or its nontoxic, pharmaceutically acceptable acid addition salts.

In its most advantageous form, the compositions in accordance with this invention will also contain a non-toxic pharmaceutical carrier in addition to the active compound.

The amount of the (−) enantiomer of trans-2-phenylcyclopropylamine or its pharmaceutically acceptable acid addition salts which can be used in the present invention is an amount which will produce anti-depressive activity, that is, an effective amount. Preferably, the composition will contain the active compound in an amount of from about 5 mg to about 150 mg and advantageously from about 10 mg to about 100 mg per dosage unit.

A wide variety of pharmaceutical forms can be employed. Thus, if a solid carrier is used, the preparation can be tabletted, placed on a hard gelatin capsule or in the form of a troche or lozenge. The amount of solid carrier will vary widely but preferably will be from about 25 mg to about 1 gm. If a liquid carrier is used, the preparation may be in the form of a soft gelatin capsule, placed in an ampule or in a liquid suspension.

The method in accordance with this invention comprises administering internally (−) trans-2-phenylcyclopropylamine or a non-toxic pharmaceutically acceptable acid addition salt thereof admixed with a suitable pharmaceutical carrier, for example, any of the above compositions. The administration may be parenterally or orally, the latter being the preferable route of administration. Advantageously equal doses will be administered one to four times daily. Preferably the daily dosage will be from about 5 mg to about 150 mg and most advantageously from about 10 mg to about 60 mg of active medicament in pharmaceutical forms.

The (−) trans-2-phenylcyclopropylamine may be prepared by known methods, e.g. U.S. Pat. No. 2,997,422 and the Kaiser et al publication supra.

Generally, the trans isomer of 2-phenylcyclopropylamine is prepared by reacting styrene with ethyl diazoacetate and forming the ester, ethyl 2-phenylcyclopropanecarboxylate. The resulting ester is hydrolyzed to the 2-phenylcyclopropanecarboxylic acid. At this stage there are 3 to 4 parts of the trans isomer to 1 part of the cis isomer. A complete separation is accomplished by recrystallizing the acid from hot water. The pure trans isomer comes out as crystalline material while the cis isomer stays in solution. The trans 2-phenylcyclopropanecarboxylic acid is then reacted with thionyl chloride to form the acid chloride which is then successively treated with sodium azide and subjected to the curtius degradation. The isocyanate formed by this procedure is hydrolyzed readily to the (+) (−) 2-phenylcyclopropylamine.

The racemic mixture can be resolved into its enantiomers with conventional resolving agents such as, for example, Camphor-10-sulfonic acid, tartaric acid, abietic acid. Generally, most optically active organic acid may be used as resolving agents provided they fulfill conventional resolution requirements, i.e., allowing for formation and cleavage of the diastereoisomers and proper crystallizing properties of the diastereoisomers, etc.

Preferably the hydrochloride salt of the (−) trans-2-phenylcyclopropylamine is used; however, either the base itself or a non-toxic, pharmaceutically acceptable acid addition salt of the base may be used, such as the salt derived from sulfuric, nitric, phosphoric, citric, acetic, lactic, mandelic, salicylic, tartaric, ethanedisulfonic, sulfamic, acetylsalicylic, succinic, fumaric, maleic, hydrobromic, benzoic and like non-toxic acids. The salts are best prepared by reacting the free base with a stoichiometric amount of the desired organic or inorganic acid in a suitable solvent such as ethyl acetate-ether solution, ethanol, acetone, water or various combinations of solvents.

Suitable formulations include the following:

Example I

| Ingredients: | Amounts, mg. |
|---|---|
| (−) Trans-2-phenylcyclopropylamine hydrochloride | 75 |
| Magnesium stearate | 2 |
| Lactose | 130 |

The above powders are thoroughly mixed and filled into a No. 2 hard gelatin capsule.

Example II

| Ingredients: | Amounts, mg. |
|---|---|
| (−) Trans-2-phenylcyclopropylamine | 50 |
| Calcium sulfate, dihydrate (terra alba) | 125 |
| Sucrose | 25 |
| Starch | 15 |
| Talc | 5 |
| Stearic acid | 3 |

The sucrose, calcium sulfate and (−) trans-2-phenylcyclopropylamine hydrochloride are thoroughly mixed, granulated with hot 10% gelatin solution. The wetted mass is passed through a No. 6 mesh screen directly onto drying tray. The granules are dried at 120° F. and passed through a 20 mesh screen. These granules are then mixed with the starch, talc and stearic acid, passed through a No. 60 mesh screen and then compressed into tablets.

Example III

| Ingredients: | Amounts, mg. |
|---|---|
| (−) Trans-2-phenylcyclopropylamine acetate | 150 |
| Magnesium stearate | 2 |
| Lactose | 125 |

The ingredients are mixed and filled into a No. 2 hard gelatin capsule.

Example IV

| Ingredients: | Amounts, mg. |
|---|---|
| (−) Trans-2-phenylcyclopropylamine maleate | 50 |
| Peanut oil | 225 |

The ingredients are mixed to a thick slurry and filled into a soft gelatin capsule.

Example V

| Ingredients: | Amounts, mg. |
|---|---|
| (−) Trans-2-phenylcyclopropylamine hydrochloride | 2.0 |
| Sodium chloride | 0.375 |
| Water for injection q.s. 100.00 ml. | |

Example VI

The following Example describes a clinical study on the effectiveness of (−) trans-2-phenylcyclopropylamine in temporarily alleviating the symptoms of depression.

10 patients with a primary diagnosis of depressive disorder were selected and were randomly assigned to either the (+) or (−) enantiomers of trans-2-phenylcyclopropylamine in such a way that they were evenly distributed. Patients over 60 years of age, those with major medical illness, or blood pressure higher than 140/90 were excluded from the study. The study was run on a double blind basis, that is, neither the patient nor the administering physician or nurse knew which of the drugs used was the (−) or (+) isomer.

Design of Drug Administration

There was a washout period lasting 3–7 days for all patients. The starting dosage was 10 mg per day for both the (+) and (−) isomer. This dosage was increased to 20 mg/day in 3 days and again to 30 mg within 1 week which was the maximum dosage used. No medications (other than sleeping pills) were simultaneously given during the trial.

Psychological Evaluations

The following scales were used. The patient's personal data inventory (PPDI), the Brief Psychiatric Rating Scale (BPRS), the Clinical Global Impressions (CGI), the Treatment Emergent Symptons (TES), the Nurses Observation Scale for Inpatient Evaluation (NOSIE), the Hamilton Depression Scale, and the Sympton Checklist 90 (SCL-90). These scales were completed at pre-treatment, day 3, day 7, day 14 and day 21.

Results

The (−) isomer of tranylcypromine was found to be more effective and produced fewer side effects than the (+) isomer of tranylcypromine.

Example VII

Effect of (+) trans-2-phenylcyclopropylamine (Tranylcypromine) and its (+) and (−) optical isomers on the Pressor response to tyramine in the anesthetized rat.

The purpose of this study is to demonstrate the differences between the (+) and (−) isomers and (±) racemate of tranylcypromine in their ability to potentiate the hypertensive effect of tyramine in rats.

Methods

Male, albino, Charles River strain rats weighing between 350 and 500 grams were used in these studies. The rats were pretreated orally with various doses of the (+) isomer, (−) isomer or the (±) racemate. Eighteen hours following treatment, the rats were anesthetized with an intravenous dose of 45.0 mg/kg of Pentobarbital sodium. The intravenous injection was performed using the rat tail vein. After anesthesia was achieved, 0.5 cc of normal saline was used to flush the needle and short catheter of Pentobarbital. The needle and catheter remained in place to allow for administration of the subsequent tyramine challenge. A vertical incision was made along the midline of the neck and the underlying muscle was separated and the right carotid artery was isolated. The vagus nerve was separated from the artery and the artery was canulated with a catheter filled with sodium heparin. The catheter was attached to a pressure transducer, which in turn was plugged into an electronic recorder.

After the blood pressure stabilized for 2–5 minutes, the rat was injected with 0.04 mg/kg of tyramine. The blood pressure was monitored until the peak pressor response to the tyramine challenge subsided.

Tranylcypromine and its isomers were dissolved in water. The concentration of each solution was adjusted so that each rat received 1.0 cc per 100.0 grams of body weight orally. The tyramine was dissolved in water at a concentration of 0.25 mg per cc of solution. Each rat received 0.02 cc of this solution per 100.0 grams of body weight, intravenously.

a. Acute

Groups of rats (n = 8) were pretreated with a single dose of (+), (−) and (±) tranylcypromine and mean peak increases in blood pressure were observed after administration of tyramine. The results are shown in Table 1 below.

Table 1

Effect of Pretreatment with (±), (+), or (−) Tranylcypromine on Anesthetized Rats Blood Pressure Response to Intravenous Administration of 0.04 mg/kg of Tyramine

| Treatment | Base Dose | N | Pre-Tyramine Blood Pressure x ±S.D. (mmHg) x ± S.D. (mmHg) | Δ Blood Pressure Produced by Tyramine |
|---|---|---|---|---|
| Controls | — | 28 | 129±14.5 | +9.4±3.0 |
| (±) tranylcypromine (18 hr pretreatment) | 0.366 mg/kg | 8 | 135±14.5 | +16.9±3.6 |
|  | 0.731 mg/kg | 8 | 126±11.9 | +25.6±9.2 |
|  | 1.46 mg/kg | 8 | 119±24.0 | +38.2±10.9 |
| (+) tranylcypromine (18 hr pretreatment) | 0.366 mg/kg | 8 | 129±15.8 | +18.1±3.1 |
|  | 0.731 mg/kg | 8 | 111±13.2 | +34.9±9.2 |
|  | 1.46 mg/kg | 8 | 102±17.2 | +39.5±8.2 |
| (−) tranylcypromine (18 hr pretreatment) | 0.366 mg/kg | 8 | 127±9.6 | +10.1±3.1 |
|  | 0.731 mg/kg | 8 | 128±15.6 | +13.7±2.8 |
|  | 1.46 mg/kg | 8 | 128±17.2 | +16.6±5.3 |

Table 1 shows that moderate doses of the (−) isomer (0.366 mg/kg and 0.731 mg/kg) do not significantly affect blood pressure while the same doses of (+) isomer and (±) racemate do significantly raise the blood pressure of the test animals. That is, the mean peak increases in the blood pressure of the control group was 9.4 and the mean peak increases in the blood pressure found with the 0.366 and 0.731 mg/kg doses of the (−) isomer was 10.1 and 13.7, indicating that there was no significant change. In comparison, at the same dose levels, the (+) isomer produced significant mean peak increases in blood pressure of 18.1 and 34.9 and the (±) racemate produced significant mean peak increases in blood pressures of 16.9 and 25.6. At a higher dose of 1.46 mg/kg, the (−) isomer showed a relatively small mean peak increase in pressure of 16.6 compared to 39.5 for the (+) isomer and 38.2 for the (±) racemate.

b. Chronic

Groups of rate (n = 6) were pretreated with (−) and (±) tranylcypromine at indicated doses for 4 consecutive days. Eighteen hours following the last treatment, the rats were challenged with the indicated dose of tyramine. The results are shown in Table below.

Table 2

Effect of Pretreatment with the (±) Racemate and the (−) Isomer of Tranylcypromine for Four Consecutive Days on the Pressor Response to Tyramine

| Treatment | Base Dose | N | Pre-Tyramine Blood Pressure x ± S.D. (mmHg) | Δ Blood Pressure Produced by Tyramine x ± S.D. (mmHg) |
|---|---|---|---|---|
| (±) tranylcypromine | 0.366 mg/kg/day | 6 | 123±16.5 | 24.5±5.6 |
| (−) tranylcypromine | 0.731 mg/kg/day | 6 | 128±16.5 | 15.7±3.7 |
|  | 1.46 mg/kg/day | 6 | 131±14.8 | 21.8±3.3 |

Table 2 shows that at chronic doses of 0.366 mg/kg, the mean peak increase in blood pressure of the (±) racemate was 24.5 while that of the (−) isomer at twice the concentration was only 15.7 and at four times the concentration only 21.8.

Tables 1 and 2 combined show that the mean peak increase in blood pressure of the (±) racemate of tranylcypromine given chronically was significantly greater than the increase obtained as a result of a single dose at the same concentration (24.5 vs 16.9), while the mean peak increase in blood pressure of the (−) isomer given chronically was only slightly higher than the increase obtained as a result of a single dose at the same concentration (15.7 vs 13.7 and 21.8 vs 16.5)

In summary, the foregoing study shows that the (+) isomer of tranylcypromine shows slightly, but significantly more hypertensive side effects than the (±) racemate while the (−) isomer shows significantly less hypertensive side effects than the (±) racemate or the (+) isomer. On the whole, the data show that the (±) racemate and (+) isomer of trans-2-phenylcyclopropylamine have approximately 4 times the hypertensive effect of the (−) isomer in rats challenged with tyramine.

I claim:

1. A method for temporarily alleviating the symptoms of depression in humans comprising internally administering to humans suffering from depression a composition comprising an effective amount of a compound selected from the group consisting of (−) trans-2-phenylcyclopropylamine and a non-toxic pharmaceutically acceptable acid addition salt thereof, said composition being substantially free of (+) trans-2-phenylcyclopropylamine.

2. The method of claim 1 wherein the composition additionally contains a suitable pharmaceutical carrier.

3. The method of claim 1 wherein an effective amount of compound is about 5 to about 150 mg.

4. The method of claim 1 wherein the compound is administered in a daily dosage regimen of from about 5 mg to about 150 mg.

5. The method of claim 1 wherein the compound is administered orally one to four times daily in a dosage unit of from about 10 mg to about 60 mg.

6. The method of claim 1 wherein the compound is (−) trans-2-phenylcyclopropylamine sulfate.

7. A method for temporarily alleviating the symptoms of depression in humans comprising internally administering to humans suffering from depression about 5 mg to about 150 mg of a compound selected from the group consisting of (−) trans-2-phenylcyclopropylamine and a non-toxic pharmaceutically acceptable addition salt thereof, together with a pharmaceutical carrier, said composition being substantially free of (+) trans-2-phenylcyclopropylamine.

8. The method of claim 7 wherein the compound is administered in a daily dosage regimen of from about 5 mg to about 150 mg.

9. The method of claim 7 wherein the compound is administered orally one to four times daily in a dosage unit of from about 10 mg to about 60 mg.

10. The method of claim 7 wherein the compound is (−) trans-2-phenylcyclopropylamine sulfate.

* * * * *